(12) United States Patent
Sue

(10) Patent No.: US 6,412,489 B1
(45) Date of Patent: Jul. 2, 2002

(54) ORAL DEVICE FOR PROMOTING NOSE BREATHING

(76) Inventor: Steven K. Sue, P.O. Box 10515, Honolulu, HI (US) 96816

(*) Notice: Subject to any disclaimer, the term of this patent is extended or adjusted under 35 U.S.C. 154(b) by 0 days.

(21) Appl. No.: 09/784,113

(22) Filed: Feb. 16, 2001

(51) Int. Cl.$^7$ .................................................. A61F 5/56
(52) U.S. Cl. ........................ 128/848; 128/859; 128/861
(58) Field of Search ................................. 128/846, 848, 128/859–862; 602/902; 433/6

(56) References Cited

U.S. PATENT DOCUMENTS

| | | | |
|---|---|---|---|
| 1,302,004 A | | 4/1919 | Brown |
| 3,871,370 A | * | 3/1975 | McDonald .................. 128/860 |
| 4,718,662 A | * | 1/1988 | North .......................... 128/860 |
| 5,447,168 A | * | 9/1995 | Bancroft ..................... 128/859 |
| 5,566,684 A | | 10/1996 | Wagner |
| 5,692,523 A | | 12/1997 | Croll et al. |
| 5,732,715 A | | 3/1998 | Jacobs et al. |
| 5,931,164 A | | 8/1999 | Kiely et al. |
| 5,941,246 A | | 8/1999 | Roopchand |
| 6,053,168 A | * | 4/2000 | Sue ............................. 128/860 |
| 6,244,865 B1 | * | 6/2001 | Nelson ........................ 128/860 |
| 6,295,988 B1 | * | 10/2001 | Sue ............................. 128/861 |

* cited by examiner

*Primary Examiner*—Michael A. Brown
(74) *Attorney, Agent, or Firm*—Siemens Patent Services, LC

(57) ABSTRACT

An oral device for holding the tongue pressed against the roof of the mouth, thereby promoting suction closing the lips and encouraging breathing through the nose. The device has a U-shaped front wall extending along the exterior surface of the user's upper and lower teeth, and a tongue supporting platform projecting horizontally and rearwardly from the front wall. The tongue supporting platform is located substantially midway between the top and bottom surfaces of the front wall. In one embodiment, the tongue supporting platform is continuous along the interior surface of the front wall. In another embodiment, the tongue supporting platform is discontinuous, having a right side section and a left side section, and being absent at the center of the front wall. In still another embodiment, the oral device has a forwardly projecting handle.

7 Claims, 1 Drawing Sheet

ORAL DEVICE FOR PROMOTING NOSE BREATHING

BACKGROUND OF THE INVENTION

1. Field of the Invention

The present invention relates to physiological devices worn within the mouth for supporting the tongue and lips in appropriate positions for promoting breathing through the nose. The device assists those who fail to breathe through the nose to learn to do so and routinely breathe in this manner.

2. Description of the Prior Art

The tongue, lips, and other parts of the mouth exert significant influences on breathing and ancillary functions of the body. Efficiency of breathing and air flow within the mouth and other breathing passages maximizes physiological functions, such as athletic activities and night time breathing. Breathing through the nose is a significant practice which brings about many physiological benefits. It is especially superior to breathing through the mouth in that it conserves body water supplies by minimizing evaporative losses in the mouth and throat.

Nasal breathing, if not practiced intentionally or if not established as the norm, can be encouraged by the use of a suitable device which forces the body into an appropriate condition for nasal breathing. Devices of limited similarity have been proposed for beneficial purposes other than to encourage nasal breathing, primarily as mouth guards. United U.S. Pat. No. 1,302,004, issued to Thomas W. Brown on Apr. 29, 1919, shows an early mouth protector having a horizontal, U-shaped platform, and an attached upright wall. The upright wall is limited to the front of the U-shaped platform. Such a configuration would not be suitable for the purposes of the present invention because it would not hold the tongue in a suitable position to assure proper nasal breathing.

U.S. Pat. No. 5,732,715, issued to Scott Jacobs et al., U.S. Pat. No. 5,931,164, issued to Timothy Kiely et al. on Aug. 3, 1999, and U.S. Pat. No. 5,941,246, issued to Roland Roopchand on Aug. 24, 1999, each show a mouthpiece comprising U-shaped trough or channel. By contrast, the present invention is not a trough in that it has only one upright wall rather than two such walls. A trough will fail to hold the tongue in proper position to accomplish the purposes of the invention.

U.S. Pat. No. 5,566,684, issued to Eugene C. Wagner on Oct. 22, 1996, shows a mouthguard comprising a U-shaped member having more than nominal thickness but lacking an upright wall. This wall is important in holding the tongue in proper position to function as intended.

U.S. Pat. No. 5,692,523, issued to Theodore P. Croll et al. on Dec. 2, 1997, shows a mouthguard comprising a U-shaped horizontal platform bearing an upright wall. However, this wall is perforated by openings which would relieve vacuum which promotes appropriate positioning of the tongue relative to the gums and teeth, and which would further enable breathing through the mouth. The device of Croll et al. is formed in two separable parts, unlike that of the present invention.

None of the above inventions and patents, taken either singly or in combination, is seen to describe the instant invention as claimed.

SUMMARY OF THE INVENTION

The present invention provides an oral device for supporting the tongue in a suitable position for maintaining sealing of the lips and mouth, as would be appropriate for breathing through the nose. The novel oral device seals the mouth when the mouth is closed thereover. The device holds the tongue in a position establishing an effective seal under these conditions. The tongue is held in a position against the roof of the mouth, thereby establishing an effective seal preventing or severely limiting passage of air into the breathing passages through the mouth, by mild suction naturally occurring between the tongue and the roof of the mouth. The user is obliged to breath through the nose.

Structure of the device includes a vertical U-shaped front wall and a horizontal platform which supports the tongue. The horizontal platform extends horizontally and rearwardly from the vertical wall. The vertical wall is positioned to the outside of the teeth, as the device is worn, and prevents insertion of the device deep into the mouth by interfering abutment with the teeth. In alternative embodiments, the platform may be U-shaped, conforming in configuration to the U-shaped upright wall, or may be abbreviated so that it is not continuous along the full length of the upright wall. In a further alternative embodiment, the device incorporates a handle projecting to the front. This embodiment is intended for the very young, who may require that the device be placed in the mouth by others.

The device is formed from a form holding yet flexible material which assures that it will fit closely to the mouth.

Accordingly, it is a principal object of the invention to provide an oral device which encourages and promotes breathing through the nose.

It is another object of the invention to hold the tongue in a position wherein it naturally seals the mouth against air flow, and is held in place by naturally occurring suction.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
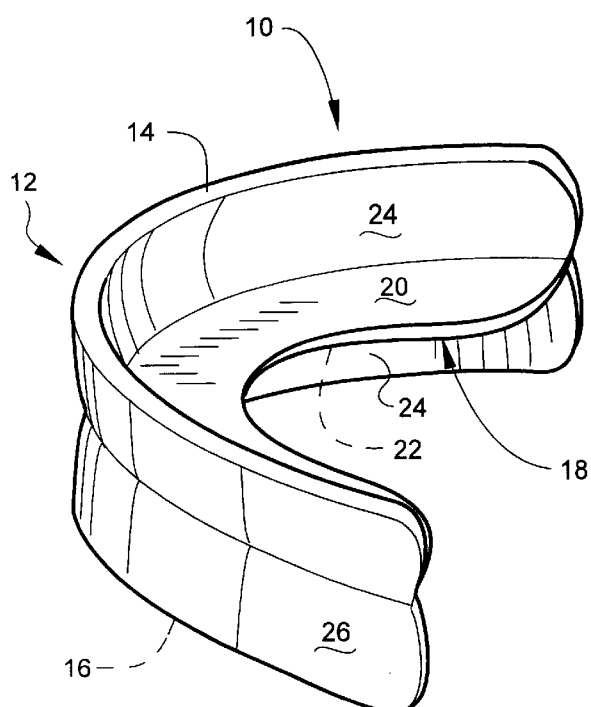
FIG. 1 is a perspective view of an embodiment of the invention.

Turning now to FIG. 1, there is shown an oral device 10 for promoting nasal breathing by positioning a user's tongue in sealing contact with the hard palate (the user's anatomy is not shown). Device 10 comprises a generally vertical U-shaped front wall 12 having an upper edge or surface 14 and a corresponding lower edge or surface 16, and a tongue platform 18.

Tongue platform 18 is fixed to and projects horizontally and rearwardly from front wall 12. Tongue platform 18 is located substantially midway between upper surface 14 and lower surface 16 of front wall 12. Tongue platform 18 has a flat upper surface 20 and a corresponding flat lower surface 22, both of which surfaces 20, 22 are open to the rear of the mouth. For purposes of this discussion, the front of device 10 is that side visible from an observer facing the user's face. The rear is that side relatively closer to the rear of the user's head.

Front wall 12 has a generally smooth interior surface 24 and a generally smooth exterior surface 26 both above and below tongue platform 18. This characteristic enables device 10 to be premanufactured in a selection of sizes, and need not be formed according to anatomy of each individual patient. Therefore, mass production and marketing techniques may be exploited. Surface 24 is dimensioned and configured to encircle or surround the user's upper teeth and lower teeth laterally from the exterior of the teeth.

Surface 24 and front wall 12 are further configured to be continuous and imperforate from surface 14 to surface 16, to obstruct flow of air from the user's mouth when the user's mouth is closed over device 10. This feature prevents relief of natural vacuum which occurs when the tongue is projected forwardly against the upper teeth, as is appropriate when breathing through the nose. In this situation, interior surface 24 of front wall 12 abuts the upper and lower teeth.

Figure 2:
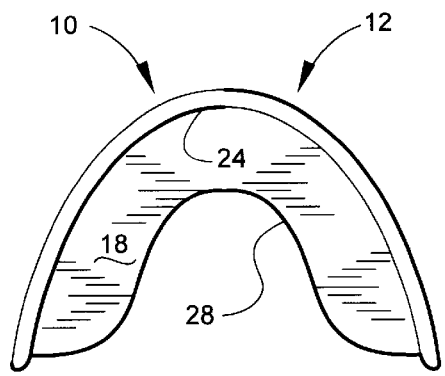
FIG. 2 is a top plan view of FIG. 1.

In the embodiment of FIG. 1, tongue platform 18 is U-shaped when viewed in plan, as clearly shown in FIG. 2. A U-shaped relief 28 defines the rear or interior configuration of platform 18. This configuration makes it easy for the user to place his or her tongue into operative position resting on tongue platform 18. Tongue platform 18 extends continuously along interior surface 24 of front wall 12. This configuration promotes appropriate forward projection of the tongue in most people. More specifically, the tongue is held against the roof of the hard and soft palates.

Figure 3:
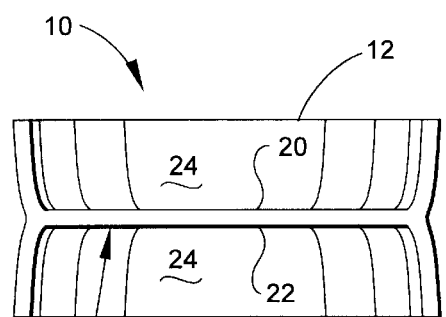
FIG. 3 is a rear elevational view of FIG. 1

The embodiment of FIG. 1 is also shown in FIG. 3, wherein it will be seen that tongue platform 18 is generally straight and flat along upper and lower surfaces 20, 22. Also, tongue platform 18 divides front wall 12 into upper and lower sections of generally equal height such that front wall 12 is sufficiently high to cover both the upper teeth and the lower teeth when the user's mouth is closed over device 10. Proportions thusly defined are not critical, but correlate to relative heights of the upper and lower teeth of most people. This enables device 10 to be worn comfortably in the mouth, thereby helping to overcome any inclination to avoid using device 10.

Figure 4:
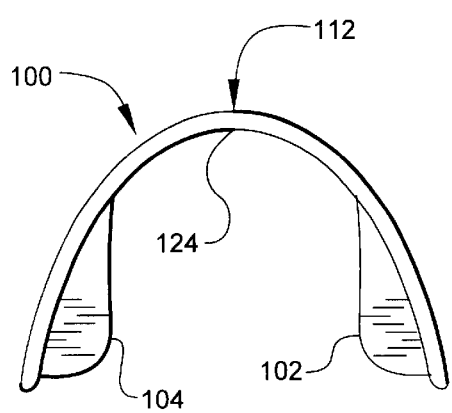
FIG. 4 is top plan view of an alternative embodiment of the invention.

As seen in FIG. 4, in another embodiment, the tongue platform of an otherwise similar oral device 100 has separated right and left support shelves 102, 104 fixed to and projecting horizontally from the interior surface 124 of front wall 112 near the rearmost parts of front wall 112. Alternatively stated, the tongue platform of the embodiment of FIG. 4 is discontinuous along interior surface 124 of front wall 112. Orientation of shelves 102, 104 with respect to front wall 112 is otherwise similar to the embodiment of FIG. 1. The embodiment of FIG. 4 is desirable for use with the young, who are possibly susceptible to incorrectly positioning the tongue. Patients too young to talk cannot be questioned as to positioning of the tongue. Hence it is desirable to promote correct usage by virtue of configuration of the device.

Figure 5:
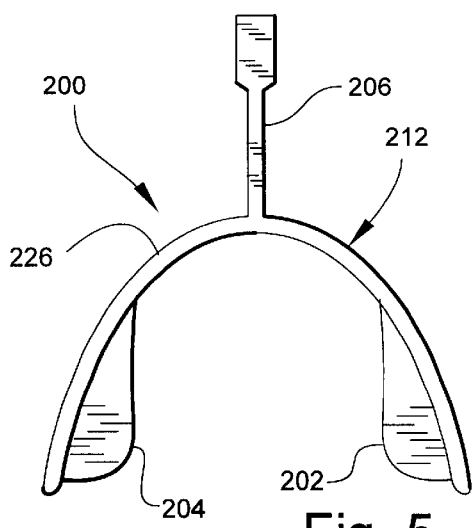
FIG. 5 is a top plan view of another alternative embodiment of the invention.

Referring now to FIG. 5, a further alternative embodiment is shown wherein oral device 200 has a handle 206 attached to exterior surface 226 of front wall 212. Handle 206 preferably includes a loop (not shown), a "tee", or other structure enabling effective grasping by finger. Handle 206 assists in preventing the young from swallowing the device, and further serves as visual indication that the device is being used. Device 200 has a tongue platform comprising separated right and left support shelves 202, 204, in the manner of the embodiment of FIG. 4. Of course, the embodiment of FIG. 1 could be modified to include a handle comparable to that of FIG. 5.

The various embodiments of the invention are formed from a partially rigid synthetic material. The material is sufficiently flexible to bend under manual pressure, but partially rigid in that it will hold its configuration absent manual or equivalent pressure acting to deform its configuration as shown in the drawings. Suitable materials may be selected from silicones and synthetic resins, including those conventionally employed to form castings and impressions for dental and other purposes. A preferred synthetic material is silicone rubber. Flexibility of this material imparts comfort to the user. Another material found suitable for the application is ethyl vinyl acetate (EVA).

The present invention is susceptible to variations and modifications which may be introduced without departing from the inventive concept. Illustratively, any embodiment of the invention need not extend the full length of the teeth from right molar to left molar. It need only extend sufficient length to resist being readily dislodged from its proper, effective position within the mouth.

Effective position implies that natural tongue thrusting, and sucking and chewing in infants, naturally propel the tongue to the roof of the mouth. This will cause the device to operate automatically, thereby providing benefits including overcoming poor craniofacial development, crooked teeth, in some cases allergies and watery or itchy eyes, snoring, hyperventilation, rapid heart beat, anxiety, fatigue, restlessness, in some cases asthma, and others detrimental conditions.

It is to be understood that the present invention is not limited to the embodiments described above, but encompasses any and all embodiments within the scope of the following claims.

I claim:

1. An oral device for promoting nasal breathing by positioning a user's tongue in sealing contact with the hard palate, comprising
  a vertical U-shaped front wall having a generally smooth interior surface, a generally smooth exterior surface, an upper surface, and a lower surface, wherein said interior surface is dimensioned and configured to surround the user's upper teeth and lower teeth, and to obstruct flow of air from the user's mouth when the user's mouth is closed over said oral device with said interior surface abutting the upper and lower teeth, and
  a tongue platform fixed to and projecting horizontally and rearwardly from said front wall, wherein said tongue platform is located substantially midway between said upper surface and said lower surface of said front wall, wherein said tongue platform has a flat upper surface open to the rear of the mouth and a flat lower surface open to the rear of the mouth.

2. The oral device according to claim 1, wherein said tongue platform is U-shaped, and extends continuously along said interior surface of said front wall.

3. The oral device according to claim 1, wherein said tongue platform is discontinuous along said interior surface of said front wall, and includes separated right and left horizontal support shelves.

4. The oral device according to claim 3, further comprising a handle attached to said exterior surface of said front wall.

5. The oral device according to claim 1, wherein said front wall is sufficiently high to cover both the upper teeth and the lower teeth when the user's mouth is closed over said oral device.

6. The oral device according to claim 1, wherein said oral device is formed from a partially rigid synthetic material which has sufficient rigidity such that said oral device avoids spontaneous slumping and like deformation, and which has sufficient flexibility such that said oral device bends readily when subjected to manual forces.

7. The oral device according to claim 6, wherein said synthetic material is one from the group silicone rubber and ethyl vinyl acetate.

* * * * *